United States Patent [19]

Domagala et al.

[11] Patent Number: 4,771,055

[45] Date of Patent: Sep. 13, 1988

[54] 7-[[3-(AMINOMETHYL)-3-ALKYL]-1-PYR-ROLIDINYL]-QUINOLINE-CARBOXYLIC ACIDS

[75] Inventors: John M. Domagala, Canton; Susan E. Hagen, Ypsilanti; Joseph P. Sanchez, Canton, all of Mich.

[73] Assignee: Warner-Lambert Company, Morris Plains, N.J.

[21] Appl. No.: 39,438

[22] Filed: Apr. 21, 1987

Related U.S. Application Data

[63] Continuation-in-part of Ser. No. 889,994, Jul. 28, 1986, abandoned.

[51] Int. Cl.[4] .................... C07D 215/56; A61K 31/47
[52] U.S. Cl. .................................. 514/312; 546/123; 546/156; 548/566; 562/433; 260/544 R
[58] Field of Search .......................... 514/312; 546/156

[56] References Cited

U.S. PATENT DOCUMENTS 4,665,079  5/1987  Culbertson et al. ................ 546/156

FOREIGN PATENT DOCUMENTS

| 106489 | 4/1984 | European Pat. Off. . |
| 132845 | 2/1985 | European Pat. Off. . |
| 153163 | 8/1985 | European Pat. Off. ............ 514/312 |
| 154780 | 9/1985 | European Pat. Off. . |
| 172651 | 2/1986 | European Pat. Off. . |
| 126082 | 6/1986 | Japan . |

OTHER PUBLICATIONS

Chemical Abstracts No. 196274s, vol. 106 for JP 30776, (2/9/87).
Chemical Abstract for Japan Kokai 61,126,082, (6/13/86), Matsumoto et al., #106:4995h, (1987).

*Primary Examiner*—Donald G. Daus
*Assistant Examiner*—E. Bernhardt
*Attorney, Agent, or Firm*—Ronald A. Daignault

[57] ABSTRACT

Novel, orally active antibacterial agents are described and characterized as 7-[[3-(aminomethyl)-3-alkyl]-1-pyrrolidinyl]-6-fluoro-1,4-dihydro-4-oxo-3-quinoline carboxylic acids or corresponding 1,8-naphthyridine derivatives as well as methods for their manufacture.

20 Claims, No Drawings

7-[[3-(AMINOMETHYL)-3-ALKYL]-1-PYR-ROLIDINYL]-QUINOLINE-CARBOXYLIC ACIDS

CROSS-REFERENCE TO RELATED APPLICATION

This application is a continuation-in-part of U.S. application Ser. No. 889,994, filed July 28, 1986, now abandoned.

BACKGROUND OF THE INVENTION

European Patent Publication Nos. 106,489 and 153,163 describe 7-(3-aminomethyl-1-pyrrolidinyl)-1,4-dihydro-4-oxo-quinolines and naphthyridines as antibacterial agents. The corresponding 5-amino compounds are described in European Patent Publication No. 172,651. Corresponding 1-aryl derivatives are described in U.S. application Ser. No. 695,145 of Jan. 25, 1985.

European Patent Publication No. 132,845 describes 7-(3-amino-1-pyrrolidinyl)-6-fluoro-1-cyclopropyl-1,4-dihydro-4-oxo-1,8-naphthyridine-3-carboxylic acids where the pyrrolidine ring may be further substituted by alkyl groups as antibacterial agents.

It has now been found that corresponding 7-[[3-(aminomethyl)-3-alkyl]-1-pyrrolidinyl quinoline and naphthyridine derivatives of the present invention have the same potent antibacterial activity against both gram-positive and -negative bacteria as the described compounds but, in addition, surprisingly have better oral activity against both gram-positive and -negative bacteria.

SUMMARY OF THE INVENTION

Accordingly, the present invention relates to a compound of the formula

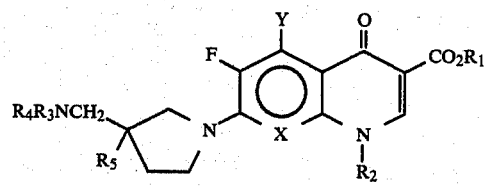

wherein X is CH, CF, CCl, CNR$_3$R$_4$, or N; Y is H, OR$_4$, or —NR$_3$R$_4$; R$_1$ is hydrogen or alkyl having from one to six carbon atoms; R$_2$ is cyclopropyl or aryl; R$_3$ is hydrogen, alkyl having from one to three carbon atoms or cycloalkyl having from three to six carbon atoms; R$_4$ is hydrogen or alkyl having from one to three carbon atoms; and R$_5$ is alkyl having from one to three carbon atoms or cycloalkyl having from three to six carbon atoms, or a pharmaceutically acceptable acid addition or base salt thereof.

The invention also includes a pharmaceutical composition which comprises an antibacterially effective amount of a compound having structural Formula I and the pharmaceutically acceptable salts thereof in combination with a pharmaceutically acceptable carrier.

The invention further includes a method for treating bacterial infections in a mammal which comprises administering an antibacterially effective amount of the above defined pharmaceutical composition to a mammal in need thereof.

DESCRIPTION OF THE PREFERRED EMBODIMENTS

The term, aryl, is intended to include a phenyl group unsubstituted or substituted by halogen, alkyl, alkoxy, hydroxy, amino, monoalkylamino, dialkylamino, or trifluoromethyl. Preferred subsitutents are in the para-position and are fluoro, amino, monoalkyl, or dialkylamino. Most preferred is the para-fluoro substituent.

The alkyl groups contemplated by the invention comprise both straight and branched carbon chains of from one to about six carbon atoms unless otherwise stated. Representative of such groups are methyl, ethyl, propyl, isopropyl, and the like.

The cycloalkyl groups contemplated by the invention comprise those having three to six carbon atoms such as cyclopropyl, cyclobutyl, cyclopentyl, and cyclohexyl.

The alkoxy groups contemplated by the invention comprise both straight and branched carbon chains of from one to about six carbon atoms unless otherwise specified. Representative of such groups are methoxy, ethoxy, propoxy, i-propoxy, t-butoxy, hexoxy, and the like.

The terms monoalkylamino and dialkylamino are intended to include amino substituted by one or two alkyl groups as defined above where each group is the same or different. Representative of such groups are methylamino, ethylamino, dimethylamino, diethylamino, methylethylamino, and the like.

The term halogen is intended to include fluorine, chlorine, bromine, and iodine unless otherwise specified.

The compounds of the invention exist in optically active forms. The pure R isomer, pure S isomer as well as mixtures thereof; including the racemic mixtures, are contemplated by the invention. Additional assymmetric carbon atoms may be present in a substituent such as an alkyl group. All such isomers as well as mixtures thereof are intended to be included in the invention.

The compounds of the invention are capable of forming both pharmaceutically acceptable acid addition and/or base salts. Base salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine.

Pharmaceutically acceptable acid addition salts are formed with organic and inorganic acids.

Examples of suitable acids for salt formation are hydrochloric, sulfuric, phosphoric, acetic, citric, oxalic, malonic, salicyclic, malic, gluconic, fumaric, succinic, ascorbic, maleic, lactic, methanesulfonic, and the like. The salts are prepared by contacting the free base form with a sufficient amount of the desired acid to produce either a mono or di, etc, salt in the conventional manner. The free base forms may be regenerated by treating the salt form with a base. For example, dilute solutions of aqueous base may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention. Use of excess base where R' is hydrogen gives the corresponding basic salt.

The compounds of the invention can exist in unsolvated as well as solvated forms, including hydrated forms. In general, the solvated forms, including hydrated forms and the like are equivalent to the unsolvated forms for purposes of the invention.

Preferred compounds of the present invention are those of Formula I wherein X is CH, CF, CCl, $CNR_3R_4$, or N; Y is H, $OR_4$, or $-NR_3R_4$; $R_1$ is hydrogen; $R_2$ is cyclopropyl, phenyl or phenyl substituted by halogen, alkyl, alkoxy, hydroxy, amino, monoalkylamino, dialkylamino, or trifluoromethyl; $R_3$ and $R_4$ are each independently hydrogen or alkyl of one to three carbon atoms; and $R_5$ is alkyl of one to three carbon atoms, or pharmaceutically acceptable acid addition or base salts thereof.

Other preferred compounds of the present invention are those of Formula I, as defined above, wherein $R_2$ is cyclopropyl, phenyl or phenyl substituted in the para-position by fluoro, amino, monoalkyl- or dialkylamino.

Still other preferred compounds of the present invention are those of Formula I, as defined above, wherein $R_2$ is cyclopropyl, phenyl, or para-fluorophenyl.

Further preferred compounds of the present invention are those of Formula I, wherein X is CH, CF, CCl, $CNH_2$, or N; Y is hydrogen or amino; $R_1$ is hydrogen; $R_2$ is cyclopropyl; $R_3$ and $R_4$ are each independently hydrogen, methyl or ethyl, and $R_5$ is methyl, or pharmaceutically acceptable acid addition or base salts thereof.

Particularly valuable as orally active antibacterial agents are the following:

7-[[3-(aminomethyl)-3-methyl]-1-pyrrolidinyl]-1-cyclopropyl-6,8-difluoro-1,4-dihydro-4-oxo-3-quinolinecarboxylic acid;

5-amino-7-[[3-(aminomethyl)-3-methyl]-1-pyrrolidinyl]-1-cyclopropyl-6,8-difluoro-1,4-dihydro-4-oxo-3-quinolinecarboxylic acid;

7-[[3-(aminomethyl)-3-methyl]-1-pyrrolidinyl]-1-cyclopropyl-6-fluoro-1,4-dihydro-4-oxo-1,8-naphthyridine-3-carboxylic acid;

7-[[3-(aminomethyl)-3-methyl]-1-pyrrolidinyl]-8-chloro-1-cyclopropyl-6-fluoro-1,4-dihydro-4-oxo-3-quinolinecarboxylic acid;

8-amino-7-[[3-(aminomethyl)-3-methyl]-1-pyrrolidinyl]-1-cyclopropyl-6-fluoro-1,4-dihydro-4-oxo-3-quinolinecarboxylic acid;

1-cyclopropyl-6,8-difluoro-1,4-dihydro-7-[3-methyl-3-[(methylamino)methyl]-1-pyrrolidinyl]-4-oxo-3-quinolinecarboxylic acid;

1-cyclopropyl-6-fluoro-1,4-dihydro-7-[3-methyl-3-[(methylamino)methyl]-1-pyrrolidinyl]-4-oxo-1,8-naphthyridine-3-carboxylic acid;

8-chloro-1-cyclopropyl-6-fluoro-1,4-dihydro-7-[3-methyl-3-[(methylamino)methyl]-1-pyrrolidinyl]-4-oxo-3-quinolinecarboxylic acid;

8-amino-1-cyclopropyl-6-fluoro-1,4-dihydro-7-[3-methyl-3-[(methylamino)methyl]-1-pyrrolidinyl]-4-oxo-3-quinolinecarboxylic acid;

7-[[3-(aminomethyl)-3-methyl]-1-pyrrolidinyl]-1-cyclopropyl-6-fluoro-1,4-dihydro-4-oxo-3-quinolinecarboxylic acid;

1-cyclopropyl-7-[3-[(dimethylamino)methyl]-3-methyl-1-pyrrolidinyl]-6,8-difluoro-1,4-dihydro-4-oxo-3-quinolinecarboxylic acid;

1-cyclopropyl-7-[3-[(dimethylamino)methyl]-3-methyl-1-pyrrolidinyl]-6-fluoro-1,4-dihydro-4-oxo-1,8-naphthyridine-3-carboxylic acid;

8-chloro-1-cyclopropyl-7-[3-[(dimethylamino)methyl]-3-methyl-1-pyrrolidinyl]-6-fluoro-1,4-dihydro-4-oxo-3-quninolinecarboxylic acid;

8-amino-1-cyclopropyl-7-[3-[(dimethylamino)methyl]-3-methyl-1-pyrrolidinyl]-6-fluoro-1,4-dihydro-4-oxo-3-quinolinecarboxylic acid;

1-cyclopropyl-7-[3-[(dimethylamino)methyl]-3-methyl-1-pyrrolidinyl]-6-fluoro-1,4-dihydro-4-oxo-3-quinolinecarboxylic acid; and 1-cyclopropyl-6-fluoro-1,4-dihydro-7-[3-methyl-[(methylamino)methyl]-1-pyrrolidinyl]-4-oxo-3-quinolinecarboxylic acid.

The compounds of the present invention and of Formula I may be prepared by reacting a compound of the formula

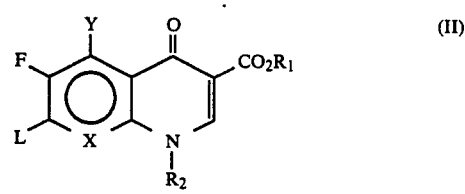

wherein X, Y, $R_1$, and $R_2$ are as defined above and L is a leaving group which is preferably fluorine or chlorine with an amine of the formula

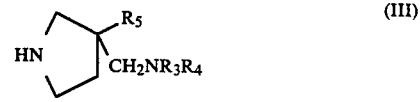

in which $R_3$, $R_4$ and $R_5$ are as defined above.

For purposes of this reaction, the aminomethyl or alkylaminomethyl substituent of Compound III may, if desired, be protected by a group which renders it substantially inert to the reaction conditions. Thus, for example, protecting groups such as the following may be utilized: carboxylic acyl groups such as formyl, acetyl, trifluoroacetyl; alkoxycarbonyl groups such as ethoxycarbonyl, t-butoxycarbonyl, $\beta,\beta,\beta$-trichloroethoxycarbonyl, $\beta$-iodoethoxycarbonyl; aryloxycarbonyl groups such as benzyloxycarbonyl, p-methoxybenzyloxycarbonyl, phenoxycarbonyl; silyl groups such as trimethysilyl; and groups such as trityl, tetrahydropyranyl, vinyloxycarbonyl, o-nitrophenylsulfenyl, diphenylphosphinyl, p-toluenesulfonyl, and benzyl, may all be utilized. The protecting group may be removed, after the reaction between Compound III and Compound II if desired, by procedures known to those skilled in the art. For example, the ethoxycarbonyl group may be removed by acid or base hydrolysis and the trityl group may be removed by hydrogenolysis.

The reaction between the compound of structural Formula II and a compound of Formula III or a suitably protected compound of Formula III, may be performed with or without a solvent, preferably at elevated temperature for a sufficient time so that the reaction is substantially complete. The reaction is preferably carried out in the presence of an acid acceptor such as an alkali metal or alkaline earth metal carbonate or bicarbonate, a tertiary amine such as triethylamine, pyridine, or picoline. Alternatively an excess of the compound of Formula III may be utilized as the acid acceptor.

Convenient solvents for this reaction are nonreactive solvents such as acetonitrile, tetrahydrofuran, ethanol, chloroform, dimethylsulfoxide, dimethylformamide, dimethylacetamide, pyridine, picoline, water, and the like. Solvent mixtures may also be utilized.

Convenient reaction temperatures are in the range of from about 20° to about 150° C.; higher temperatures usually require shorter reaction times.

The starting compounds having structural Formula II are known in the art (see the references cited in the Background of the Invention section herein) or, if new, may be prepared from known starting materials by standard procedures or by variations thereof.

The compounds of Formula II wherein Y is —NR$_3$R$_4$ and R$_3$ and/or R$_4$ are not hydrogen may be prepared from the known 5-amino quinolines or naphthyridines by an alkylation sequence shown below wherein L is a leaving group as previously defined.

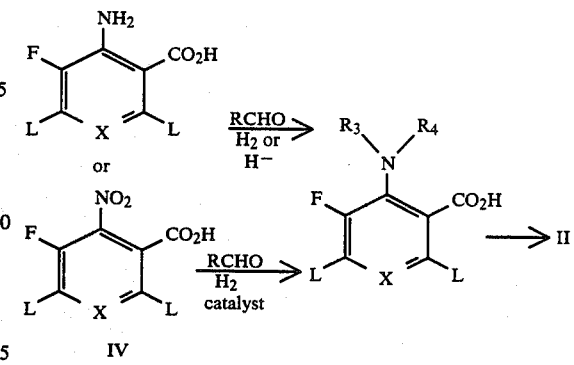

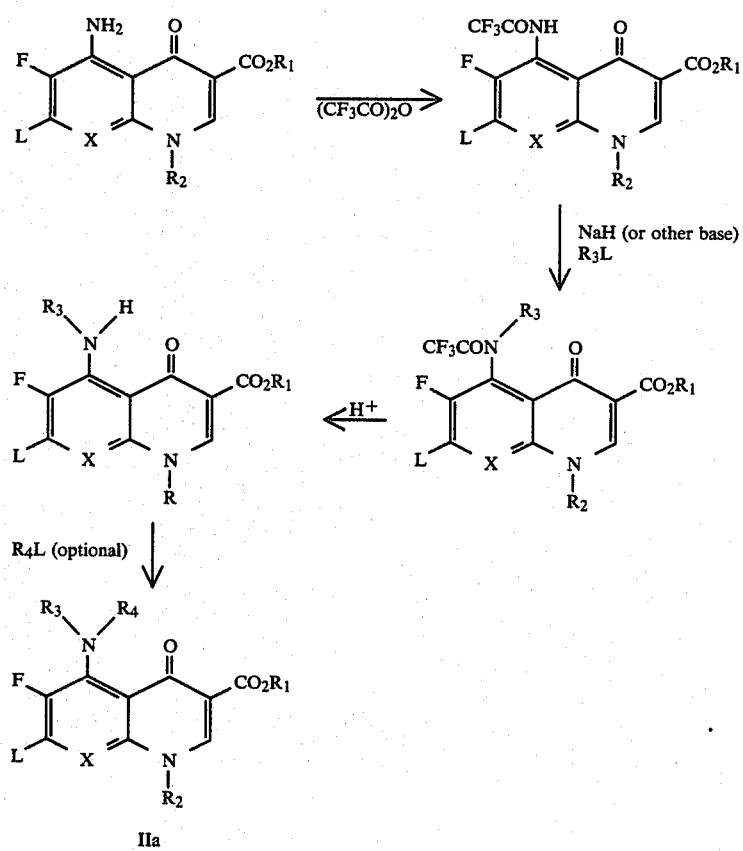

The 5-amino group is preferably acylated by trifluoroacetic acid anhydride although other acyl moieties may be employed. The alkylation of R$_3$ proceeds with the presence of sodium hydride or other nonnucleophilic bases. Removal of the acyl activating group is accomplished with acid or base hydrolysis such as 2N hydrochloric acid in acetic acid. A second alkylation, if desired, with R$_4$L, again in the presence of base such as, for example, potassium carbonate provides compounds of Formula II where both R$_3$ and R$_4$ are not hydrogen.

Alternatively, the 5-alkylamino compounds of Formula II may be prepared from the nitro or amino acids IV through reductive amination procedures as illustrated in the following scheme. Using appropriate control of the aldehyde equivalents mono and disubstituted amines may be obtained. The substituted amino acids may be converted to the desired compounds of Formula II by methods described in the references cited in the Background of the Invention.

The compounds of Formula II wherein Y is OR$_4$ may be prepared from the polysubstituted acids or esters by displacement of an ortho leaving group with OR$_4$ as shown:

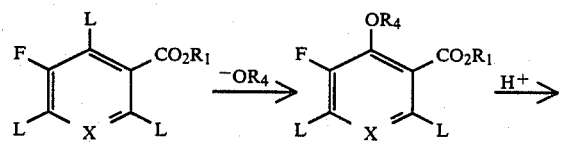

-continued

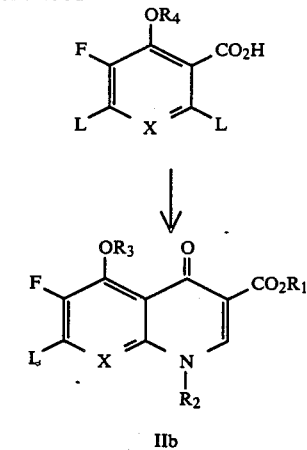

IIb

The desired quinolines or naphthyridines of Formula II may then be prepared according to the general methods described in the references cited in the Background of the Invention.

The compounds of Formula III are new and may be prepared according to the following general method.

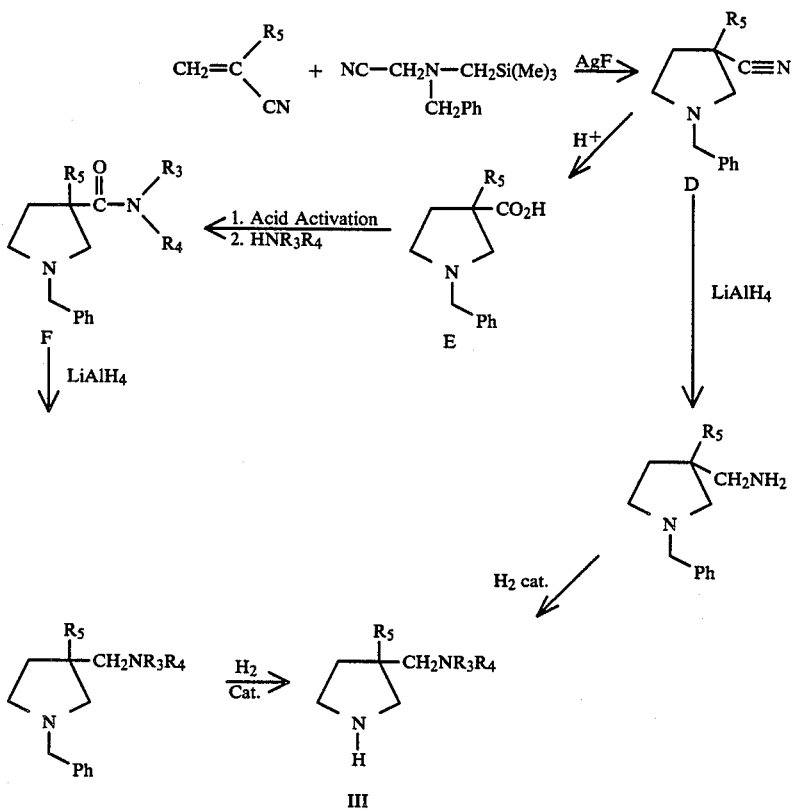

III

Pyrrolidine formation to D may be carried out by the known methods, [J. Org. Chem., 50 4006 (1985)]. When $R_3$ and $R_4$ are H, direct reduction of D with a strong reducing agent, for example, lithium aluminum hydride, and catalytic hydrogenation affords III ($R_3R_4=H$). When $R_3$ and $R_4$ are not both hydrogen, then hydrolysis of nitrile D to the acid E is accomplished with strong acid as, for example, 6N HCl.

Using any of the methods available to one skilled in the art, the acid function of E may be activated via acid chloride formation, mixed anhydride formation, ester formation, or with dicyclohexylcarbodiimide or N,N'-carbonyldiimidazole as examples. The activated acid is then coupled with an amine $HNR_3R_4$ to form the amide F. Reduction and removal of the benzyl protective group affords compounds of Formula III where $R_3$ and $R_4$ are not both hydrogen.

The compounds of the invention display potent antibacterial activity against both gram-positive and -negative bacteria when tested by the microtitration dilution method as described in Heifetz, et al, Antimicr. Agents & Chemoth., 6, 124 (1974), which is incorporated herein by reference.

The advantage of the compounds of the present invention has been observed when tested orally and compared to a standard quinolone where the 7-position contains a corresponding 3-aminomethylpyrrolidinyl group without the additional 3-alkyl or cycloalkyl substituent. For example, the compound of Example 1 when compared to 7-[3-(aminomethyl)-1-pyrrolidinyl]-1-cyclopropyl-6,8-difluoro-1,4-dihydro-4-oxo-3-quinolinecarboxylic acid, Compound A in the table below, has comparable in vitro activity but greater oral activity in mice when the measurement of $PD_{50}$, mouse protection data, was carried out according to the procedure described below.

Therapeutic activities of the compounds were compared to acute mouse protection tests in which 18- to 22-g female Charles River CD-1 mice were used. Oral or subcutaneous doses in twofold rising incremental series were administered concurrently with bacterial challenge. Challenges were accomplished by the intraperitoneal injection of an estimated 100 medial lethal doses in 0.5 ml volumes of 5% hog gastric mucin or tryptic soy broth. Generally, >90% of the untreated controls died within 48 to 72 hours. Final survival percentages, obtained after four to seven days of observation among groups of 8 to 16 mice, were pooled and used to estimate median protective doses (PD$_{50}$) by the log-probit method. Ideally a PO/SC ratio for a therapeutically relevant antibacterial should be ≦5. Table 2 indicates the improvement in PO/SC ratio.

TABLE 1

IN VITRO ANTIBACTERIAL ACTIVITY
Minimal Inhibitory Concentration
MIC (μg/ml)

| Organisms | Compound Ex. 1 | Compound Ex. 2 | Compound Ex. 3 | Compound Ex. 4 | Compound Ex. A |
|---|---|---|---|---|---|
| *Enterobacter cloacae* MA 2646 | .025 | .1 | .1 | .05 | .8 |
| *Escherichia coli* Vogel | .05 | .1 | .4 | .025 | .2 |
| *Klebsiella pneumoniae* MGH-2 | .1 | .1 | .2 | .05 | .4 |
| *Proteus rettgeri* M 1771 | .2 | .4 | .8 | .1 | .8 |
| *Pseudomonas aeruginosa* UI-18 | .4 | .8 | .8 | .2 | .8 |
| *Staphylococcus aureus* H 228 | .013 | .013 | .05 | .013 | .1 |
| *Staphylococcus aureus* UC-76 | ≦.003 | ≦.003 | .013 | ≦.003 | .013 |
| *Streptococcus faecalis* MGH-2 | .013 | .025 | .05 | .013 | .1 |
| *Streptococcus pneumoniae* SV-1 | .006 | ≦.003 | .025 | ≦.003 | .012 |
| *Streptococcus pyogenes* C-203 | .025 | .013 | .05 | .013 | .012 |

TABLE 2

MOUSE CHEMOTHERAPY RESULTS
Protective Dose 50%
PD$_{50}$ (mg/kg)

| | Organism | | | | | | | | |
|---|---|---|---|---|---|---|---|---|---|
| | E. coli | | P. aerug. | | S. aureus | | S. pyog. | | PO/SC |
| Compound | PO | SC | PO | SC | PO | SC | PO | SC | Ratio |
| A | 13 | 1 | >100 | 3 | 10 | 1 | 4 | 0.4 | ≧10 |
| Example 1 | 2 | 1 | 38 | 18 | 5 | 2 | 9 | 3 | ≦3 |

The compounds of the invention may be prepared and administered in a wide variety of oral, parenteral, topical, and ophthalmic dosage forms. It will be obvious to those skilled in the art that the following dosage forms may comprise as the active component, either a compound of Formula I or a corresponding pharmaceutically acceptable salt of a compound of Formula I. Because of the superior oral activity of the compounds of the present invention, oral dosage forms are obviously preferred for administration.

For preparing pharmaceutical compositions from the compounds described by this invention, inert, pharmaceutically acceptable carriers can be either solid or liquid. Solid form preparations include powders, tablets, dispersable granules, capsules, cachets, suppositories, and ointments. A solid carrier can be one or more substances which may also act as diluents, flavoring agents, solubilizers, lubricants, suspending agents, binders, or tablets disintegrating agents; it can also be an encapsulating material. In powders, the carrier is a finely divided solid which is in admixture with the finely divided solid which is in admixture with the finely divided active compound. In the table the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium sterate, talc, sugar, lactose, pectin, dextrin, starch, gelatin, tragacanth, methyl cellulose, sodium carboxymethyl cellulose, a lower melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Liquid form preparations include solutions suspensions and emulsions. As an example may be mentioned water or water-propylene glycol solutions for parenteral injection. Such solutions are prepared so as to be acceptable to biological systems (isotonicity, pH, etc). Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspension suitable for oral use can be made by dispersing the finely divided active component in water with viscous material, i.e., natural or synthetic gums, resins, methyl cellulose, sodium carboxymethyl cellulose, and other well-known suspending agents.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, powders in vials or ampoules, and ointments in tubes or jars. The unit dosage form can also be a capsule, cachet, tablet, gel or cream itself or it can be the appropriate number of any of these packaged forms.

The quantity of active compound in a unit dose of preparation may be varied or adjusted from 1 mg to 100 mg according to the particular application and the potency of the active ingredient.

In therapeutic use as agents for treating bacterial infections the compounds utilized in the pharmaceuticaly method of this invention are administered at the initial dosage of about 3 mg to about 40 mg per kilogram daily. A daily dose range of about 6 mg to about 14 mg per kilogram is preferred. The dosages, however, may be varied depending upon the requirements of the patient, the severity of the condition being treated, and the compound being employed. Determination of the proper dosage for a particular situation is within the skill or the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting examples illustrate the inventor' preferred methods for preparing the compounds of the invention.

EXAMPLE 1

7-[[3-(Aminomethyl)-3-methyl]-1-pyrrolidinyl]-1-cyclopropyl-6,8-difluoro-1,4-dihydro-4-oxo-3-quinolinecarboxylic acid A suspension of 1.0 g (3.53 mmol) of 1-cyclopropyl-6,7,8-trifluoro-1,4-dihydro-4-oxo-3-quinolinecarboxylic acid, 40 ml of acetonitrile, 1.0 g (9.9 mmol) of triethylamine, and 0.70 g (6.15 mmol) of 3-methyl-3-pyrrolidinemethanamine was refluxed for five hours, then stirred at room temperature overnight. The precipitate was removed by filtration and washed with ether to give 1.25 g of the title compound, mp 245°-247° C.

EXAMPLE 2

5-Amino-7-[[3-(aminomethyl)-3-methyl]-1-pyrrolidinyl]-1-cyclopropyl-6,8-difluoro-1,4-dihydro-4-oxo-3-quinolinecarboxylic acid A suspension of 0.60 g (2.01 mmol) of 5-amino-1-cyclopropyl-6,7,8-trifluoro-1,4-dihydro-4-oxo-3-quinolinecarboxylic acid, 50 ml of acetonitrile, 0.60 g (6.0 mmol) of triethylamine, and 0.30 g (2.63 mmol) of 3-methyl-3-pyrrolidinemethanamine was refluxed for six hours, then stirred at room temperature overnight. The precipitate was removed by filtration and washed with ether to give 0.40 g of the title compound, mp 201°-204° C.

EXAMPLE 3

7-[[3-(Aminomethyl)-3-methyl]-1-pyrrolidinyl]-1-cyclopropyl-6-fluoro-1,4-dihydro-4-oxo-1,8-naphthyridine-3-carboxylic acid To 1.0 g (3.6 mmol) of 7-chloro-1-cyclopropyl-6-fluoro-1,4-dihydro-4-oxo-1,8-naphthyridine-3-carboxylic acid was added 12 ml of acetonitrile. One gram (9.9 mmol) of triethylamine and 0.7 g (6.1 mmol) of 3-methyl-3-pyrrolidinemethanamine. The mixture was refluxed for three hours, cooled, and filtered to give 1.18 g of the title compound, mp 257°-259° C.

EXAMPLE 4

7-[3-(Aminomethyl)-3-methyl-1-pyrrolidinyl]-8-chloro-1-cyclopropyl-6-fluoro-1,4-dihydro-4-oxo-3-quinolinecarboxylic acid To 1.05 g (3.50 mmol) of 8-chloro-1-cyclopropyl-6,7-difluoro-1,4-dihydro-4-oxo-3-quinolinecarboxylic acid was added 15 ml of acetonitrile, 1.0 g (9.9 mmol) of triethylamine and 0.7 g (6 mmol) of the 3-methyl-3-pyrrolidinemethanamine. The mixture was refluxed 18 hours and cooled. Filtration gave 1.31 g of the title compound, mp 189°-191° C.

In a similar manner, the following were prepared: 7-[[3-(aminomethyl)-3-methyl]-1-pyrrolidinyl]-1-cyclopropyl-6-fluoro-1,4-dihydro-4-oxo-3-quinolinecarboxylic acid, mp 250°-252° C.; 1-cyclopropyl-7-[3-[(dimethylamino)methyl]-3-methyl-1-pyrrolidinyl)-6-fluoro-1,4-dihydro-4-oxo-3-quinolinecarboxylic acid, and 1-cyclopropyl-7-[3-[(dimethylamino)methyl]-3-methyl-1-pyrrolidinyl]-6-fluoro-1,4-dihydro-4-oxo-1,8-naphthyridine-3-carboxylic acid.

In a similar manner 7-[[3-(aminomethyl)-3-methyl]-1-pyrrolidinyl]-1-cyclopropyl-6,8-difluoro-1,4-dihydro-5-methylamino-4-oxo-3-quinolinecarboxylic acid, 7-[[3-(aminomethyl)-3-methyl]-1-pyrrolidinyl]-1-cyclopropyl-6,8-difluoro-1,4-dihydro-5-dimethylamino-4-oxo-3-quinolinecarboxylic acid and 7-[[3-(aminomethyl)-3-methyl]-1-pyrrolidinyl]-1-cyclopropyl-6,8-difluoro-1,4-dihydro-5-methoxy-4-oxo-3-quinolinecarboxylic acid, are prepared from the 3-methyl-3-pyrrolidinemethanamine and the appropriate quinoline starting material.

Preparation of Starting Materials

EXAMPLE A

3-Methyl-1-(phenylmethyl)-3-pyrrolidinecarbonitrile

A suspension of 11.6 g (0.05 mole) of N-benzyl-N-(cyanomethyl)-N-[(trimethylsilyl)methyl]amine [*J. Org. Chem.*, 50, 4006 (1985)], 3.5 g (0.052 mole) of methacrylonitrile, 7.0 g (0.55 mole) of silver fluoride, and 150 ml of acetonitrile was stirred overnight at room temperature in the dark. The mixture was then diluted with chloroform (150 ml) and filtered through Celite. Concentration of the filtrate gave an oil which was subjected to silica gel chromatography using an 80:20 chloroform:ethyl acetate mixture as the eluent. The major fraction contained 2.5 g of the titled compound.

EXAMPLE B

3-Methyl-1-(phenylmethyl)-3-pyrrolidinemethanamine

To a solution of 2.0 g (10 mmol) of 3-methyl-1-(phenylmethyl)-3-pyrrolidinecarbonitrile in 40 ml tetrahydrofuran was added 0.38 g (10 mmol) of lithium aluminum hydride in portions under nitrogen. The reaction mixture was stirred at room temperature for 18 hours. To the resulting suspension were added 0.3 ml of water, 0.4 ml of 40% sodium hydroxide, and 1.4 ml of water. The grainy precipitate was filtered and washed with tetrahydrofuran. The combined filtrates were concentrated to yield 1.9 g of the titled compound.

This material was used without further purification in the next step, see Example C.

EXAMPLE C

3-Methyl-3-pyrrolidinemethanamine

A suspension of 1.87 g (9 mmol) of 3-methyl-1-(phenylmethyl)-3-pyrrolidinemethanamine, 1.0 g of 20% palladium on carbon, and 100 ml of methanol was shaken in an atmosphere of hydrogen at about 50 psi and at room temperature for 18 hours. The catalyst was filtered and the filtrate concentrated under reduced pressure to give 1.0 g of the titled compound.

EXAMPLE D

N,N,3-Trimethyl-3-pyrrolidinemethanamine

To 2.0 g (10 mmol) of 3-methyl-1-(phenylmethyl)-3-pyrrolidinecarbonitrile was added 25 ml of 6N HCl and the mixture refluxed for 36 hours. It was concentrated to dryness and the residue was dissolved in water and the pH adjusted to 9.0. The water was extracted three times with dichloromethane. The water layer was then taken to pH 5.5 and the product was extracted into dichloromethane which was dried (MgSO₄) and concentrated. The compound was treated with an excess of oxalyl chloride in 25 ml of tetrahydrofuran with 1.0 ml of dimethylformamide added. When gas evolution was complete excess dimethylamine was added to form the N,N-3-trimethyl-1-(phenylmethyl)-3-pyrrolidinecarboxamide which was located as a viscous oil from concentration and water workup. The crude product was then reduced using lithium aluminum hydride and deprotected with hydrogenation as described in Examples B and C to give the title compound which was purified by distillation. In a similar fashion, N,3-dimethyl-3-pyrrolidinemethanamine was also prepared.

EXAMPLE E

1-Cyclopropyl-6,7,8-trifluoro-1,4-dihydro-5-(methylamino)-4-oxo-3-quinolinecarboxylic acid A solution of 5.9 g (20 mmol) of 5-amino-1-cyclopropyl-6,7,8-trifluoro-1,4-dihydro-4-oxo-3-quinolinecarboxylic acid, 20 ml of trifluoroacetic anhydride, and 100 ml of trifluoro acetic acid was stirred at room temperature overnight. The solution was evaporated to dryness and the residue was triturated with water and filtered to give 7.55 g of 1-cyclopropyl-6,7,8-trifluoro-1,4-dihydro-4-oxo-5-[(trifluoroacetyl)amino]-3-quinolinecarboxylic acid, mp 188°.

A solution of 5.53 (14.0 mmol) of the trifluoroacetyl intermediate above, 55 ml of DMF and 1.42 g (30.9 mmol) of 50% sodium hydride was stirred at 50°-55° for 35 minutes. To this mixture was added 2.8 ml (45 mmol) of iodomethane with continued stirring at 50°-55° for two hours and for three hours at room temperature. The reaction mixture was evaporated and the residue was triturated with water and filtered. The solid was dissolved with 60 ml of acetic acid and 30 ml of 6N HCl was added and the solution was heated under reflux for two hours. The solution was concentrated and the residual oil was treated with isopropanol to give 3.0 g of the title compound, mp 205°-7°.

EXAMPLE F

1-Cyclopropyl-6,7,8-trifluoro-1,4-dihydro-5-dimethylamino-4-oxo-3-quinolinecarboxylic acid 2-(Dimethylamino)-3,4,5,6-tetrafluorobenzoic acid A solution of 10.0 g (41.8 mmol) of 2-nitro-3,4,5,6-tetrafluorobenzoic acid, 10 ml of 37% formaldehyde solution, 1.5 g of Raney nickel and 100 ml of ethanol was hydrogenated until TLC indicated absence of starting material. The reaction mixture was filtered and evaporated to an oil which was recrystallized with ethylacetate-hexane to give 2.15 g of the title compound, mp 110°-112°. An additional 2.28 g, mp 90°-100° was isolated from the filtrate.

2-(Dimethylamino)-3,4,5,6-tetrafluorobenzoyl chloride

To a suspension of 4.22 g (17.8 mmol) of 2-(dimethylamino)-3,4,5,6-tetrafluoro-benzoic acid and 85 ml of dichloromethane, added 1.7 ml (19.5 mmol) of oxalyl chloride. After the bubbling subsided, five drops of DMF was added and the solution was stirred at room temperature for 21 hours. The solution was evaporated to 4.8 g of an oil which was used in the next step without purification.

2-(Dimethylamino)-3,4,5,6-tetrafluoro-β-oxo-benzenepropanoic acid, ethyl ester

To a solution of 4.76 g (36 mmol) of malonic acid monoethyl ester and 75 ml of THF at −35° was added 25 ml (40 mmol) of 1.5N n-butyl lithium solution. The remaining 25 ml (40 mmol) of 1.5N butyllithium solution was added at 0°. After cooling to −78°, a solution of the 4.8 g of 2-(dimethylamino)-3,4,5,6-tetrafluorobenzoyl chloride in 50 ml of THF was added to the dilithio malonate over a 15 minute period. The reaction mixture was stirred for 1.75 hours while the temperature came up to −30°. The reaction mixture was poured into ice, water, and 50 ml of 1N HCl. The mixture was extracted with ether and the ether extract was washed with $H_2O$, 5% $NaHCO_3$, and HCl. After drying over $MgSO_4$ the ether solution was concentrated to 4.4 g of oily product. NMR spectra indicated the desired product.

2-(Dimethylamino)-α-(ethoxymethylene)-3,4,5,6-tetrafluoro-β-oxo-benzenepropanoic acid, ethyl ester A solution of 4.4 g (14.3 mmol) of the crude ketoester, 3.57 ml (21.5 mmol) of triethylorthoformate, and 25 ml of acetic anhydride was heated under reflux for two hours. The solution was evaporated to 5.2 g of oil which was used in the next step without purification.

α-[(Cyclopropylamino)methylene]-2-(dimethylamino)-3,4,5,6-tetrafluoro-β-oxo-benzenepropanoic acid, ethyl ester To a solution of 5.2 g (14.3 mmol) of the above crude product in 50 ml of t-butanol was added 1.2 ml (17 mmol) of cyclopropylamine. The reaction solution was stirred for 18 hours at room temperature. The reaction mixture was filtered to give 0.12 g of the title compound, mp 122°-4°. TLC of the filtrate showed it to be the same as the solid.

5-(Dimethylamino)-1-cyclopropyl-6,7,8-trifluoro-1,4-dihydro-4-oxo-quinolinecarboxylic acid To the above filtrate was added 1.7 g (15 mmol) of potassium t-butoxide and the mixture was stirred at room temperature for 1.5 hours. TLC showed no change in reactants. An additional 1.7 g (15 mmol) of potassium t-butoxide was added and the reaction mixture was heated at 50°-55° for two hours. After TLC indicated the reaction was complete, the solution was evaporated to 4 g of an oil. This oil was heated with 100 l 6N HCl for three hours on the steam bath. The solution was evaporated and the residue was recrystallized from isopropanol to give 0.3 g of the title compound, mp 160°-3°. An additional 1.0 g of solid was added from the filtrate.

EXAMPLE G

1-Cyclopropyl-6,7,8-trifluoro-1,4-dihydro-5-methoxy-4-oxo-3-quinolinecarboxylic acid To 22.4 g (100 mmol) of the 2-methoxy-3,4,5,6-tetrafluorobenzoic acid prepared as in [J. Fluorine Chem., 28 361 (1985)] was added 400 ml of tetrahydrofuran, 1 ml of dimethylformamide, and 13 ml of oxalylchloride. The acid chloride mixture as concentrated, diluted with 100 ml of tetrahydrofuran, and added to a solution of the dilithio anion of malonic acid monoethylester (200 mmol) in 800 ml of tetrahydrofuran at −70° C. The reaction was stirred for one hour at −30° C., poured over ice and dilute hydrochloric acid and taken into dichloromethane. The product was isolated by an extraction at pH 7, followed by drying the dichloromethane ($MgSO_4$) and concentration. The crude product was then treated neat with 2.5 equivalents of triethylorthoformate and 2.8 equivalents of acetic anhydride at 150° for two hours. The mixture was concentrated and at room temperature a slight excess of cyclopropylamine (6.0 g) was added in 50 ml of t-butanol. The mixture was stirred overnight. To this mixture was added 11.3 g of potassium t-butoxide and the temperature brought to 50° C. The mixture was concentrated after 18 hours and the residue treated with 100 ml of acetic acid and 100 ml of 4N hydrochloric acid. From this mixture after four hours at 100° C., 12.7 g of the title compound precipitated.

We claim:

1. A compound of the formula

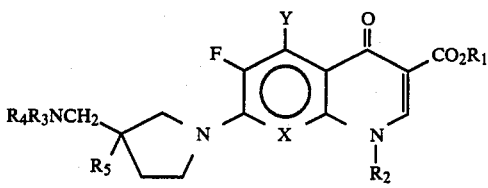

wherein X is CH, CF, CCl, or $CNR_3R_4$; Y is H, $OR_4$ or $-NR_3R_4$; $R_1$ is hydrogen or alkyl from one to six carbon atoms; $R_2$ is cyclopropyl or phenyl or phenyl substituted by halogen, lower alkyl, lower alkoxy, hydroxy, amino, monoloweralkylamino, diloweralkylamino, or trifluoromethyl; $R_3$ is hydrogen, alkyl from one to three carbon atoms or cycloalkyl from three to six carbon atoms; $R_4$ is hydrogen or alkyl from one to three carbon atoms; and $R_5$ is alkyl from one to three carbon atoms or cycloalkyl from three to six carbon atoms; or a pharmaceutically acceptable acid addition or base salt thereof.

2. A compound according to claim 1, wherein Y is H, $OR_4$ or $-NR_3R_4$; $R_1$ is hydrogen; $R_2$ is cyclopropyl, phenyl or phenyl substituted by halogen, lower alkyl, lower alkoxy, hydroxy, amino, monoloweralkylamino, diloweralkylamino, or trifluoromethyl; $R_3$ and $R_4$ are each independently hydrogen or alkyl of one to three carbon atoms; and $R_5$ is alkyl of one to three carbon atoms.

3. A compound according to claim 2, wherein $R_2$ is cyclopropyl, phenyl or phenyl substituted in the para-position by fluoro, amino, monoloweralkyl or diloweralkylamino.

4. A compound according to claim 3, wherein $R_2$ is cyclopropyl, phenyl or para-fluorophenyl.

5. A compound according to claim 4, wherein X is CH, CF, CCl OR, $CNH_2$; Y is hydrogen or amino; $R_2$ is cyclopropyl; $R_3$ and $R_4$ are each independently hydrogen, methyl or ethyl, and $R_5$ is methyl.

6. A compound according to claim 5, and being 7-[[3-aminomethyl)-3-methyl]-1-pyrrolidinyl]-1-cyclopropyl-6,8-difluoro-1,4-dihydro-4-oxo-3-quinolinecarboxylic acid.

7. A compound according to claim 5, and being 5-amino-7-[[3-(aminomethyl)-3-methyl]-1-pyrrolidinyl]-1-cyclopropyl-6,8-difluoro-1,4-dihydro-4-oxo-3-quinolinecarboxylic acid.

8. A compound according to claim 5 and being 7-[[3-(aminomethyl)-3-methyl]-1-pyrrolidinyl]-8-chloro-1-cyclopropyl-6-fluoro-1,4-dihydro-4-oxo-3-quinolinecarboxylic acid.

9. A compound according to claim 5 and being 8-amino-7-[[3-(aminomethyl)-3-methyl]-1-pyrrolidinyl]-1-cyclopropyl-6-fluoro-1,4-dihydro-4-oxo-3-quinolinecarboxylic acid.

10. A compound according to claim 5 and being 1-cyclopropyl-6,8-difluoro-1,4-dihydro-7-[3-methyl-3-[(methylamino)methyl]-1-pyrrolidinyl]-4-oxo-3-quinolinecarboxylic acid.

11. A compound according to claim 5 and being 8-chloro-1-cyclopropyl-6-fluoro-1,4-dihydro-7-[3-methyl-3-[(methylamino)methyl]-1-pyrrolidinyl]-4-oxo-3-quinolinecarboxylic acid.

12. A compound according to claim 5 and being 8-amino-1-cyclopropyl-6-fluoro-1,4-dihydro-7-[3-methyl-3-[(methylamino)methyl]-1-pyrrolidinyl]-4-oxo-3-quinolinecarboxylic acid.

13. A compound according to claim 5 and being 7-[[3-(aminomethyl)-3-methyl]-1-pyrrolidinyl]-1-cyclopropyl-6-fluoro-1,4-dihydro-4-oxo-3-quinolinecarboxylic acid.

14. A compound according to claim 5 and being 1-cyclopropyl-7-[3-[(dimethylamino)methyl]-3-methyl-1-pyrrolidinyl]-6,8-difluoro-1,4-dihydro-4-oxo-3-quinolinecarboxylic acid.

15. A compound according to claim 5 and being 8-chloro-1-cyclopropyl-7-[3-[(dimethylamino)methyl]-3-methyl-1-pyrrolidinyl]-6-fluoro-1,4-dihydro-4-oxo-3-quinolinecarboxylic acid.

16. A compound according to claim 5 and being 8-amino-1-cyclopropyl-7-[3-[(dimethylamino)methyl]-3-methyl-1-pyrrolidinyl]-6-fluoro-1,4-dihydro-4-oxo-3-quinolinecarboxylic acid.

17. A compound according to claim 5 and being 1-cyclopropyl-7-[3-[(dimethylamino)methyl]-3-methyl-1-pyrrolidinyl]-6-fluoro-1,4-dihydro-4-oxo-3-quinolinecarboxylic acid.

18. A compound according to claim 5 and being 1-cyclopropyl-6-fluoro-1,4-dihydro-7-[3-methyl-[(methylamino)methyl]-1-pyrrolidinyl]-4-oxo-3-quinolinecarboxylic acid.

19. A pharmaceutical composition which comprises an antibacterially effective amount of a compound according to claim 1 in combination with a pharmaceutically acceptable carrier.

20. A method for treating bacterial infections in a mammal which comprises administering an antibacterially effective amount of a pharmaceutical composition according to claim 19 to a mammal in need thereof.

* * * * *